(12) United States Patent
Sundermann et al.

(10) Patent No.: US 6,956,055 B2
(45) Date of Patent: *Oct. 18, 2005

(54) SUBSTITUTED γ-LACTONE COMPOUNDS AS NMDA-ANTAGONISTS (75) Inventors: Corinna Sundermann, Aachen (DE); Michael Przewosny, Aachen (DE); Werner Englberger, Stolberg (DE)

(73) Assignee: Grunenthal GmbH, Aachen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/751,741

(22) Filed: Jan. 5, 2004

(65) Prior Publication Data

US 2004/0171677 A1 Sep. 2, 2004

Related U.S. Application Data (63) Continuation of application No. PCT/EP02/07380, filed on Jul. 3, 2002.

(30) Foreign Application Priority Data

Jul. 5, 2001 (DE) .......................................... 101 32 725

(51) Int. Cl.$^7$ ..................... A61K 31/365; C07D 307/33
(52) U.S. Cl. .................. 514/472; 514/255.05; 514/275; 514/313; 514/336; 514/407; 544/332; 544/336; 546/159; 546/284.4; 548/371.4; 549/303; 549/321
(58) Field of Search .............................. 544/332, 336; 546/159, 284.4; 548/371.4; 549/303, 321; 514/255.05, 275, 313, 336, 407, 472

(56) References Cited

FOREIGN PATENT DOCUMENTS

| EP | 0386839 B1 | 1/1997 |
|---|---|---|
| WO | WO 97/12879 | 4/1997 |
| WO | WO 98/07704 | 2/1998 |
| WO | WO 98/42673 | 10/1998 |

OTHER PUBLICATIONS

Huang et al, Tet. Letters, vol. 41, p. 9747–9751 (2000).*
Leeson et al., "4–Amido–2carboxytetrahydrquinolines. Structure–Activity Relationships for Antagonism at the Glycine Site of the NMDA Receptor", J. Med. Chem. 35, 1992, pp. 1954–1968.

"Synthesis And Pharmacological Properties of Derivatives Of α–Amino–β–(p–Chlorobenzoyl)–Propionic Acid And α–Amino–γ–(p–Chlorophenyl)–Tetrahydrofuran–2–One", Zabska et al., Polish J. Pharmacol. Pharm, 1991, 43, pp. 271–280.

"Chemoenzymic Synthesis of Unnatural Amino Acids via Modified Claisen Rearrangement of Glycine Enolates. Approach to Morphine Synthesis", Gonzalez et al., Journal of Organic Chemistry, 1997, 62(5), pp. 1194–1195.

"Friedel–Crafts Reactions Of γ–aryl–γ–lactones", Plusquellec, Journal Chemical Research, SYNOP. 1982, pp. 46–47.

"Reactions Of Glyoxylic Acid Derivatives With Olefins: Synthesis of .Alpha.–substituted.gamma.–lactones", Plusquellec et al., Bulletin Societe Chimique De France, 1979, No. 9–10, PT 2, pp. 552–558.

"A New Synthesis Of Amino Acids. II. Amidoalkylation of Olefins With Glyoxylic Acid Derivatives", Ben–Ishai et al., Tetrahedron Lett. 1975, vol. 33, pp. 1533–1442.

"Amino Acid Synthesis II. Amidoalkylation Of Olefins With Glyoxylic Acid Derivatives", Altman et al., Tetrahedron Lett. 1975, No. 43, PP. 3737–3740.

"Relationship Between the Inhibition Constant ($K_1$) and the Concentration of Inhibitor Which Causes 50 per cent Inhibition ($I_{50}$) of an Enzymatic Reaction", Cheng et al., Biochemical Pharmacology, vol. 22, pp. 3099–3108, 1973.

2–Carboxytetrahydroquinolines. Conformational and Stereochemical Requirements for Antagonism of the Glycine Site on the NMDA Receptor, Carling et al., J. Med. Chem. 1992, 35, pp. 1942–1953.

"[$^3$H]MDL 105,519, a High–Affinity Radioligand for the N–Methyl–D–aspartate Receptor–Associated Glycine Recognition Site", Baron et al., Jnl of Pharm. And Experimental Therapeutics, 1996, pp. 62–68.

* cited by examiner

Primary Examiner—Bernard Dentz
(74) Attorney, Agent, or Firm—Perman & Green, LLP.

(57) ABSTRACT

The invention relates to substituted γ-lactone compounds, to methods for the production thereof, to medicaments containing these compounds and to the use of these compounds for producing medicaments.

44 Claims, 2 Drawing Sheets

Fig.1

Fig.2

SUBSTITUTED γ-LACTONE COMPOUNDS AS NMDA-ANTAGONISTS

This application is a continuation of PCT/EP02/07380 filed Jul. 3, 2002.

The present invention relates to substituted γ-lactone compounds, a process for the production thereof, pharmaceutical preparations containing these compounds and the use of these compounds for the production of pharmaceutical preparations.

The treatment of chronic and non-chronic pain is of great significance in medicine. There is a worldwide requirement for effective therapeutic methods for providing tailored and targeted treatment of chronic and non-chronic pain, this being taken to mean pain treatment which is effective and satisfactory from the patient's standpoint. This is clear from the large number of scientific papers relating to applied analgesia or to basic nociception research which have recently been published.

Conventional opioids, such as morphine for example, are highly effective in treating severe to extreme pain. However, the use thereof is limited by known side-effects such as respiratory depression, vomiting, sedation, constipation and development of tolerance. Moreover, they are less effective in treating neuropathic or incidental pain, which is in particular experienced by tumour patients.

Opioids exert their analgesic effect by binding to membrane receptors belonging to the family of G protein-coupled receptors. The biochemical and pharmacological characterisation of subtypes of these receptors has prompted hopes that subtype-specific opioids may have an effect/side-effect profile which differs from that of, for example, morphine. Further pharmacological investigations have now tentatively revealed the existence of various subtypes of these opioid receptors.

There are moreover further receptors and ion channels which play a substantial role in the system governing the genesis and transmission of pain. The NMDA ion channel, through which a substantial part of synaptic communication passes, is of particular significance in this connection. This channel controls the exchange of calcium ions between a neuronal cell and its environment.

The development of the patch-clamp technique has made it possible to elucidate the physiological significance of ion channel-selective substances. It has thus been possible clearly to demonstrate the effect of NMDA antagonists on the influence of calcium ions within the cell. It has also been established that these substances themselves have their own antinociceptive potential, such as for example ketamine. One important fact is that their mode of action differs greatly from that of, for example, opiates, as NMDA antagonists act directly on the cell's calcium balance, which vitally determines the transmission of pain. For the first time, it is thus also possible to treat neuropathic types of pain successfully.

Various NMDA antagonists from the group comprising tetrahydroquinoline derivatives have already been described in J. Med. Chem. (1992) 35, pages 1954–1968; J. Med. Chem. (1992) 35, pages 1942–1953 and Med. Chem. Res. (1991) 1; pages 64–73 and in EP 0 386 839, WO 97/12879, WO 98/07704 and WO 98/42673.

Numerous indications which are susceptible to treatment with NMDA antagonists are furthermore stated, inter alia also including the treatment of pain.

There is, however, still a requirement for effective NMDA antagonists which are preferably suitable for combatting pain.

One object underlying the present invention was accordingly to provide novel compounds which are in particular suitable as pharmaceutical active ingredients in pharmaceutical preparations, preferably as pharmaceutical preparations for combatting pain, in particular for the treatment of chronic or neuropathic pain. These active ingredients should moreover also be suitable for the treatment or prevention of neurodegenerative diseases, in particular of Alzheimer's disease, Parkinson's disease or Huntington's chorea, of migraine, stroke, cerebral ischaemia, cerebral infarct, cerebral oedema, schizophrenia, psychoses brought about by elevated amino acid levels, AIDS dementia, Tourette's syndrome, inflammatory and/or allergic reactions, depression, mental health conditions, epilepsy, urinary incontinence, pruritus, tinnitus, diarrhoea, for anxiolysis or for anaesthesia.

It has surprisingly been found that substituted γ-lactone compounds of the general formula I below act as NMDA antagonists by attacking the glycine-binding site of the NMDA receptor channel. They are accordingly suitable for combatting pain, in particular for combatting chronic or neuropathic pain, but also for the treatment or prevention of neurodegenerative diseases, in particular of Alzheimer's disease, Parkinson's disease or Huntington's chorea, of migraine, stroke, cerebral ischaemia, cerebral infarct, cerebral oedema, schizophrenia, psychoses brought about by elevated amino acid levels, AIDS dementia, Tourette's syndrome, inflammatory and/or allergic reactions, depression, mental health conditions, epilepsy, urinary incontinence, pruritus, tinnitus, diarrhoea, for anxiolysis or for anaesthesia.

The present invention accordingly provides substituted γ-lactone compounds of the general formula I in which $R^1$ denotes an optionally at least mono-substituted aryl or heteroaryl residue, an optionally at least mono-substituted aryl or heteroaryl residue attached via a $C_{1-6}$ alkylene group, an optionally at least mono-substituted, saturated, branched or unbranched aliphatic $C_{1-10}$ residue, an optionally at least mono-substituted, at least partially unsaturated, branched or unbranched aliphatic $C_{2-10}$ residue or an optionally at least mono-substituted, saturated or at least mono-unsaturated cycloaliphatic $C_{3-9}$ residue, preferably an optionally at least mono-substituted aryl or heteroaryl residue, particularly preferably an optionally at least mono-substituted aryl residue, $R^2$ denotes an optionally at least mono-substituted, saturated, branched or unbranched aliphatic $C_{1-10}$ residue or an optionally at least mono-substituted, at least partially unsaturated, branched or unbranched aliphatic $C_{2-10}$ residue, preferably an optionally at least mono-substituted, branched or unbranched $C_{1-6}$ alkyl residue, $R^3$ denotes an optionally at least mono-substituted aryl residue and $R^4$ denotes H, or $R^3$ and $R^4$ together denote an optionally at least mono-substituted, saturated or at least mono-unsaturated $C_{3-7}$ residue, with the proviso that the residue $R^2$ in this case denotes an optionally at least mono-substituted aryl residue, an optionally at least mono-substituted, saturated, branched or unbranched aliphatic $C_{1-10}$ residue or an optionally at least mono-substituted, at least partially unsaturated, branched or unbranched aliphatic $C_{2-10}$ residue, in the form of the racemates, diastereomers or enantiomers thereof as a free base or a corresponding physiologically acceptable salt, wherein the compounds of the general formula I, in which $R^1$ denotes a 2-, 4-, 6-trichlorophenyl or a tosyl residue, $R^2$ a methyl residue, $R^3$ a phenyl residue and $R^4$ denotes H, are excepted.

Preferred γ-lactone compounds are those of the general formula I in which the residue $R^3$ denotes an optionally at least mono-substituted aryl residue and the residue $R^4$ denotes H.

The aliphatic residues may be mono- or polysubstituted. If the aliphatic residues comprise more than one substituent, these may be identical or different and be attached both to the same and to different atoms of the aliphatic residue. The aliphatic residue is preferably selected from the group consisting of optionally at least mono-substituted methyl, ethyl, propyl, isopropyl, n-butyl, sec.-butyl, tert-butyl, n-pentyl, neopentyl, n-hexyl, n-heptyl, n-octyl, n-nonyl, n-decyl, propenyl, butenyl, pentenyl, hexenyl, heptenyl, octenyl, propynyl, butynyl, pentynyl, hexynyl, heptynyl and octynyl. The substituents are preferably selected from the group consisting of F, Cl, Br, I, $NH_2$, SH and OH.

The cycloaliphatic residues may be mono- or polysubstituted. If the cycloaliphatic residues comprise more than one substituent, these may be identical or different and be attached both to the same and to different atoms of the cycloaliphatic residue. The cycloaliphatic residue is preferably an optionally at least mono-substituted cyclopropyl, cyclobutyl, cyclopentyl, cyclohexyl, cycloheptyl, cyclopentenyl, cyclohexenyl or cycloheptenyl residue. The substituents are preferably selected from the group consisting of F, Cl, Br, I, $NH_2$, SH and OH.

For the purposes of the present invention an aryl residue is also taken to mean those aromatic hydrocarbon residues which are fused with a saturated or at least partially unsaturated hydrocarbon ring system.

A preferred aryl residue is an optionally at least mono-substituted phenyl, naphthyl or anthracenyl residue, particularly preferably an optionally mono-substituted phenyl residue.

If the aryl residue comprises more than one substituent, these may be identical or different. The substituents are preferably selected from the group consisting of F, Cl, Br, I, $NH_2$, SH, OH, $CF_3$, CN, $NO_2$, $OR^5$, $SR^5$, $NR^6R^7$ and $C_{1-6}$ alkyl, $C_{1-6}$ alkoxy, $C_{2-8}$ alkenyl, $C_{2-8}$ alkynyl, phenyl, phenoxy and benzyloxy which are unsubstituted or at least mono-substituted with F, Cl, Br, I, $NH_2$, SH, OH, $CF_3$, CN or $NO_2$, wherein $R^5$ denotes H, a $C_{1-10}$ alkyl residue, an unsubstituted aryl or heteroaryl residue or denotes an unsubstituted aryl or heteroaryl residue attached via a $C_{1-3}$ alkylene group and $R^6$ and $R^7$, identical or different, denote H, a $C_{1-10}$ alkyl residue, an unsubstituted aryl or heteroaryl residue or denote an unsubstituted aryl or heteroaryl residue attached via a $C_{1-3}$ alkylene group.

For the purposes of the present invention, a heteroaryl residue is understood to mean also those heteroaromatic, hydrocarbon residues which are fused with a saturated or at least partially unsaturated hydrocarbon ring system. The heteroaryl residue preferably contains a heteroatom selected from the group consisting of sulfur, nitrogen and oxygen.

The heteroaryl residue is preferably an optionally at least mono-substituted thiophenyl, furanyl, pyrrolyl, pyridinyl, pyrimidinyl, quinolinyl, isoquinolinyl, phthalazinyl or quinazolinyl residue. If the heteroaryl residue comprises more than one substituent, these may be identical or different. The substituents are preferably selected from the group consisting of F, Cl, Br, I, $NH_2$, SH, OH, $CF_3$, CN, $NO_2$, $OR^5$, $SR^5$, $NR^6R^7$ and $C_{1-6}$ alkyl, $C_{1-6}$ alkoxy, $C_{2-8}$ alkenyl, $C_{2-8}$ alkynyl, phenyl, phenoxy or benzyloxy which are unsubstituted or at least mono-substituted with F, Cl, Br, I, $NH_2$, SH, OH, $CF_3$, CN or $NO_2$, wherein the residues $R^5$, $R^6$ and $R^7$ have the above-stated meaning.

The following substituted γ-lactone compounds are very particularly preferred:

3-(2-Chloro-4-fluoro-phenylamino)-5-(4-fluoro-phenyl)-5-methyl-dihydro-furan-2-one, 5-Methyl-3-(4-phenoxy-phenylamino)-5-phenyl-dihydro-furan-2-one, 3-(2-Chloro-phenylamino)-5-(4-fluoro-phenyl)-5-methyl-dihydro-furan-2-one, 3-(4-Chloro-2-methyl-phenylamino)-5-methyl-5-phenyl-dihydro-furan-2-one, 3-(2,4-Dichloro-phenylamino)-5-(4-fluoro-phenyl)-5-methyl-dihydro-furan-2-one, 3-(4-Chloro-3-trifluoromethyl-phenylamino)-5-methyl-5-phenyl-dihydro-furan-2-one, 3-(2,3-Dichloro-phenylamino)-5-(4-fluoro-phenyl)-5-methyl-dihydro-furan-2-one, 3-(4-Iodo-phenylamino)-5-methyl-5-phenyl-dihydro-furan-2-one, 3-(4-Chloro-2-fluoro-phenylamino)-5-(4-fluoro-phenyl)-5-methyl-dihydro-furan-2-one, 3-(2-Chloro-4-methyl-phenylamino)-5-methyl-5-phenyl-dihydro-furan-2-one, 3-(2-Chloro-4-methyl-phenylamino)-5-(4-fluoro-phenyl)-5-methyl-dihydro-furan-2-one, 3-(3,5-Dichloro-phenylamino)-5-methyl-5-phenyl-dihydro-furan-2-one, 3-(3,5-Dichloro-phenylamino)-5-(4-fluoro-phenyl)-5-methyl-dihydro-furan-2-one, 3-(4-Bromo-2-chloro-phenylamino)-5-(4-fluoro-phenyl)-5-methyl-dihydro-furan-2-one, 4-(5-Methyl-2-oxo-5-phenyl-tetrahydro-furan-3-ylamino)-benzonitrile, 5-(4-Chloro-phenyl)-3-(4-iodo-phenylamino)-5-methyl-dihydro-furan-2-one, 5-(4-Chloro-phenyl)-3-(2,4-dichloro-phenylamino)-5-methyl-dihydro-furan-2-one, 5-(4-Chloro-phenyl)-3-(2-chloro-phenylamino)-5-methyl-dihydro-furan-2-one, 3-(4-Chloro-2-methyl-phenylamino)-5-(4-chloro-phenyl)-5-methyl-dihydro-furan-2-one, 3-(2-Chloro-4-fluoro-phenylamino)-5-(4-chloro-phenyl)-5-methyl-dihydro-furan-2-one, 3-(4-Chloro-2-fluoro-phenylamino)-5-(4-chloro-phenyl)-5-methyl-dihydro-furan-2-one, 3-(2-Chloro-4-methyl-phenylamino)-5-(4-chloro-phenyl)-5-methyl-dihydro-furan-2-one, 5-(4-Chloro-phenyl)-3-(2,3-dichloro-phenylamino)-5-methyl-dihydro-furan-2-one, 3-(4-Bromo-2-chloro-phenylamino)-5-(4-chloro-phenyl)-5-methyl-dihydro-furan-2-one, 5-(4-Chloro-phenyl)-3-(3,5-dichloro-phenylamino)-5-methyl-dihydro-furan-2-one,

3-(3,5-Dibromo-pyridin-2-ylamino)-5-methyl-5-phenyl-dihydro-furan-2-one, 5-(4-Chloro-phenyl)-3-(3,5-dichloro-pyridin-2-ylamino)-5-methyl-dihydro-furan-2-one,

5-(4-Chloro-phenyl)-5-methyl-3-(5-nitro-pyridin-2-ylamino)-dihydro-furan-2-one,
3-(3-Chloro-2-methyl-phenylamino)-5-(4-iodo-phenyl)-5-methyl-dihydro-furan-2-one,
5-(4-Bromo-phenyl)-3-(4-chloro-phenylamino)-5-methyl-dihydro-furan-2-one,
5-(3-Chloro-phenyl)-3-(4-chloro-phenylamino)-5-methyl-dihydro-furan-2-one,
3-(4-Chloro-phenylamino)-5-(4-iodo-phenyl)-5-methyl-dihydro-furan-2-one,
5-(4-Bromo-phenyl)-3-(2-iodo-phenylamino)-5-methyl-dihydro-furan-2-one,
5-(3-Chloro-phenyl)-3-(2-iodo-phenylamino)-5-methyl-dihydro-furan-2-one,
5-(4-Iodo-phenyl)-3-(2-iodo-phenylamino)-5-methyl-dihydro-furan-2-one,
3-(2,4-Difluoro-phenylamino)-5-methyl-5-naphthalen-1-yl-dihydro-furan-2-one,
5-(4-Bromo-phenyl)-3-(4-iodo-phenylamino)-5-methyl-dihydro-furan-2-one,
5-(3-Chloro-phenyl)-3-(4-iodo-phenylamino)-5-methyl-dihydro-furan-2-one,
3-(4-Iodo-phenylamino)-5-methyl-5-naphthalen-1-yl-dihydro-furan-2-one,
5-(4-Bromo-phenyl)-3-(3,5-dichloro-phenylamino)-5-methyl-dihydro-furan-2-one,
5-(3-Chloro-phenyl)-3-(3,5-dichloro-phenylamino)-5-methyl-dihydro-furan-2-one,
3-(3,5-Dichloro-phenylamino)-5-(4-iodo-phenyl)-5-methyl-dihydro-furan-2-one,
3-(3,5-Dichloro-phenylamino)-5-methyl-5-naphthalen-1-yl-dihydro-furan-2-one,
5-(3-Chloro-phenyl)-5-methyl-3-phenylamino-dihydro-furan-2-one,
3-(2-Bromo-4-methyl-phenylamino)-5-(4-iodo-phenyl)-5-methyl-dihydro-furan-2-one,
3-(2-Bromo-4-methyl-phenylamino)-5-methyl-5-naphthalen-1-yl-dihydro-furan-2-one,
3-(5-Chloro-2-methyl-phenylamino)-5-methyl-5-(5,6,7,8-tetrahydro-naphthalen-2-yl)-dihydro-furan-2-one,
3-(4-Bromo-2-fluoro-phenylamino)-5-isopropyl-5-phenyl-dihydro-furan-2-one,
5-(2,5-Dimethoxy-phenyl)-5-methyl-3-(5-trifluoromethyl-pyridin-2-ylamino)-dihydro-furan-2-one,
5-(3,5-Dimethoxy-phenyl)-5-methyl-3-(5-trifluoromethyl-pyridin-2-ylamino)-dihydro-furan-2-one,
3-(3-Bromo-5-methyl-pyridin-2-ylamino)-5-(2-methoxy-phenyl)-5-methyl-dihydro-furan-2-one,
3-(3-Bromo-5-methyl-pyridin-2-ylamino)-5-(2,5-dimethoxy-phenyl)-5-methyl-dihydro-furan-2-one,
3-(3-Bromo-5-methyl-pyridin-2-ylamino)-5-(3,5-dimethoxy-phenyl)-5-methyl-dihydro-furan-2-one,
3-(5-Bromo-3-methyl-pyridin-2-ylamino)-5-(2-methoxy-phenyl)-5-methyl-dihydro-furan-2-one,
3-(2-Chloro-pyridin-3-ylamino)-5-(2-methoxy-phenyl)-5-methyl-dihydro-furan-2-one,
3-(5-Bromo-pyridin-2-ylamino)-5-(2,5-dimethoxy-phenyl)-5-methyl-dihydro-furan-2-one,
3-(3-Chloro-5-trifluoromethyl-pyridin-2-ylamino)-5-(2,5-dimethoxy-phenyl)-5-methyl-dihydro-furan-2-one,
5-(2-Methoxy-phenyl)-5-methyl-3-(pyridin-2-ylamino)-dihydro-furan-2-one,
3-[5-(2,5-Dimethoxy-phenyl)-5-methyl-2-oxo-tetrahydro-furan-3-ylamino]-pyrazole-4-carboxylic acid ethyl ester,
3-[5-(3-Bromo-phenyl)-5-methyl-2-oxo-tetrahydro-furan-3-ylamino]-pyrazole-4-carboxylic acid ethyl ester,
3-[5-(3-Bromo-phenyl)-5-methyl-2-oxo-tetrahydro-furan-3-ylamino]-5-methylsulfanyl-pyrazole-4-carbonitrile,
3-[5-(2,5-Dimethoxy-phenyl)-5-methyl-2-oxo-tetrahydro-furan-3-ylamino]-pyrazole-4-carbonitrile,
3-(4-Bromo-pyrazol-3-ylamino)-5-(3,5-dimethoxy-phenyl)-5-methyl-dihydro-furan-2-one,
3-(4-Bromo-5-phenyl-2H-pyrazol-3-ylamino)-5-(2-methoxy-phenyl)-5-methyl-dihydro-furan-2-one,
3-(8-Hydroxy-quinolin-2-ylamino)-5-(2-methoxy-phenyl)-5-methyl-dihydro-furan-2-one,
5-(2,5-Dimethoxy-phenyl)-3-(8-hydroxy-quinolin-2-ylamino)-5-methyl-dihydro-furan-2-one,
5-(2-Methoxy-phenyl)-5-methyl-3-(pyrazin-2-ylamino)-dihydro-furan-2-one,
5-(3-Bromo-phenyl)-5-methyl-3-(4-methyl-pyrimidin-2-ylamino)-dihydro-furan-2-one,
2-[5-(3,5-Dimethoxy-phenyl)-5-methyl-2-oxo-tetrahydro-furan-3-ylamino]-4-propyl-pyrimidine-5-carboxylic acid ethyl ester,
5-(2-Methoxy-phenyl)-5-methyl-3-(pyrimidin-2-ylamino)-dihydro-furan-2-one,
3-(4-Chloro-3-trifluoromethyl-phenylamino)-5-phenyl-5-propyl-dihydro-furan-2-one,
3-(2-Chloro-phenylamino)-5-phenyl-5-propyl-dihydro-furan-2-one,
3-(2-Chloro-4-fluoro-phenylamino)-5-phenyl-5-propyl-dihydro-furan-2-one,
3-(4-Chloro-2-fluoro-phenylamino)-5-phenyl-5-propyl-dihydro-furan-2-one,
3-(2-Chloro-4-methyl-phenylamino)-5-phenyl-5-propyl-dihydro-furan-2-one,
3-(2-Oxo-5-phenyl-5-propyl-tetrahydro-furan-3-ylamino)-pyrazole-4-carboxylic acid ethyl ester,
3-(5-Hydroxy-4-phenylazo-pyrazol-3-ylamino)-5-phenyl-5-propyl-dihydro-furan-2-one,
3-(4-Bromo-5-phenyl-pyrazol-3-ylamino)-5-phenyl-5-propyl-dihydro-furan-2-one,
5-Methylsulfanyl-3-(2-oxo-5-phenyl-5-propyl-tetrahydro-furan-3-ylamino)-pyrazole-4-carbonitrile,
3-(5-Butyl-2-oxo-5-phenyl-tetrahydro-furan-3-ylamino)-pyrazole-4-carboxylic acid ethyl ester,
5-Butyl-3-(5-hydroxy-4-phenylazo-pyrazol-3-ylamino)-5-phenyl-dihydro-furan-2-one,
3-(4-Bromo-5-phenyl-pyrazol-3-ylamino)-5-butyl-5-phenyl-dihydro-furan-2-one,
3-(5-Butyl-2-oxo-5-phenyl-tetrahydro-furan-3-ylamino)-5-methylsulfanyl-pyrazole-4-carbonitrile,
3-(5-Butyl-2-oxo-5-phenyl-tetrahydro-furan-3-ylamino)-pyrazole-4-carbonitrile,
5-Butyl-3-(2-phenoxy-phenylamino)-5-phenyl-dihydro-furan-2-one,
5-Biphenyl-4-yl-3-(2,4-dichloro-phenylamino)-5-methyl-dihydro-furan-2-one,
5-Biphenyl-4-yl-3-(2-chloro-phenylamino)-5-methyl-dihydro-furan-2-one,
5-Biphenyl-4-yl-3-(2-chloro-4-fluoro-phenylamino)-5-methyl-dihydro-furan-2-one,
3-(5-Biphenyl-4-yl-5-methyl-2-oxo-tetrahydro-furan-3-ylamino)-pyrazole-4-carboxylic acid ethyl ester,
5-Biphenyl-4-yl-3-(4-bromo-5-phenyl-pyrazol-3-ylamino)-5-methyl-dihydro-furan-2-one,
3-(3,5-Dichlorophenylamino)-5-methyl-5-phenyl-dihydrofuran-2-one,
3-(3,5-Dichlorophenylamino)-5-methyl-5-o-tolyl-dihydrofuran-2-one,
3-(3,5-Dichlorophenylamino)-5-(4-fluorophenyl)-5-methyl-dihydrofuran-2-one,
5-(2-Chlorophenyl)-3-(3,5-dichlorophenylamino)-5-methyl-dihydrofuran-2-one, 5-(4-Chlorophenyl)-3-(3,5-dichlorophenylamino)-5-methyl-dihydrofuran-2-one,
5-(3-Bromophenyl)-3-(3,5-dichlorophenylamino)-5-methyl-dihydrofuran-2-one,
5-(4-Bromophenyl)-3-(3,5-dichlorophenylamino)-5-methyl-dihydrofuran-2-one,
3-(3,5-Dichlorophenylamino)-5-(4-iodophenyl)-5-methyl-dihydrofuran-2-one,
3-(3,5-Dichlorophenylamino)-5-(2-methoxyphenyl)-5-methyl-dihydrofuran-2-one,
3-(3,5-Dichlorophenylamino)-5-(3-methoxyphenyl)-5-methyl-dihydrofuran-2-one,
3-(3,5-Dichlorophenylamino)-5-(4-methoxyphenyl)-5-methyl-dihydrofuran-2-one,
3-(3,5-Dichlorophenylamino)-5-(2,4-dimethoxyphenyl)-5-methyl-dihydrofuran-2-one,
3-(3,5-Dichlorophenylamino)-5-(2,5-dimethoxyphenyl)-5-methyl-dihydrofuran-2-one,
3-(3,5-Dichlorophenylamino)-5-(3,5-dimethoxyphenyl)-5-methyl-dihydrofuran-2-one,
5-(Biphenyl-4-yl)-3-(3,5-dichlorophenylamino)-5-methyl-dihydrofuran-2-one,
3-(3,5-Dichlorophenylamino)-5-ethyl-5-phenyl-dihydrofuran-2-one,
3-(3,5-Dichlorophenylamino)-5-phenyl-5-n-propyl-dihydrofuran-2-one,
5-n-Butyl-3-(3,5-dichlorophenylamino)-5-phenyl-dihydrofuran-2-one,
3-(3,5-Dichlorophenylamino)-7a-phenyl-hexahydrobenzofuran,
3-(3,5-Dichlorophenylamino)-7a-(3-methoxy-phenyl)-hexahydrobenzofuran-2-one
and
3-(3,5-Dichlorophenylamino)-8a-(3-methoxy-phenyl)-octahydrocyclohepta[b]furan-2-one
and the respective corresponding physiologically acceptable salts thereof, in particular the hydrochlorides thereof.

The present invention also provides a process for the production of the γ-lactone compounds of the general formula I according to the invention, in which the residues $R^1$ to $R^4$ have the above-stated meaning, in accordance with which process at least one amine component of the general formula II in which the residue $R^1$ has the above-stated meaning, is reacted with glyoxalic acid, preferably in form of the monohydrate or an aqueous solution, and at least one alkene component of the general formula III in which the residues $R^2$ to $R^4$ have the above-stated meaning, in the presence of at least one organic and/or inorganic acid, preferably trifluoroacetic acid in an organic solvent to yield at least one compound of the above-stated general formula I and this is optionally purified using conventional methods and/or optionally isolated using conventional methods.

The quantities of the reaction components to be used of the general formulae II and III, the glyoxalic acid and the inorganic and/or organic acid, the temperature during the reaction and the duration of the reaction may vary. The suitable quantity of the components to be used for the particular reaction, the suitable temperature and the suitable duration of the reaction may be determined by the person skilled in the art by simple preliminary testing. The temperature during the reaction is preferably 0 to 100° C., particularly preferably 15 to 40° C. The duration of the reaction is preferably 0.25 to 12 hours.

Acetonitrile or a mixture containing acetonitrile is preferably used as a suitable solvent.

Figure 1:
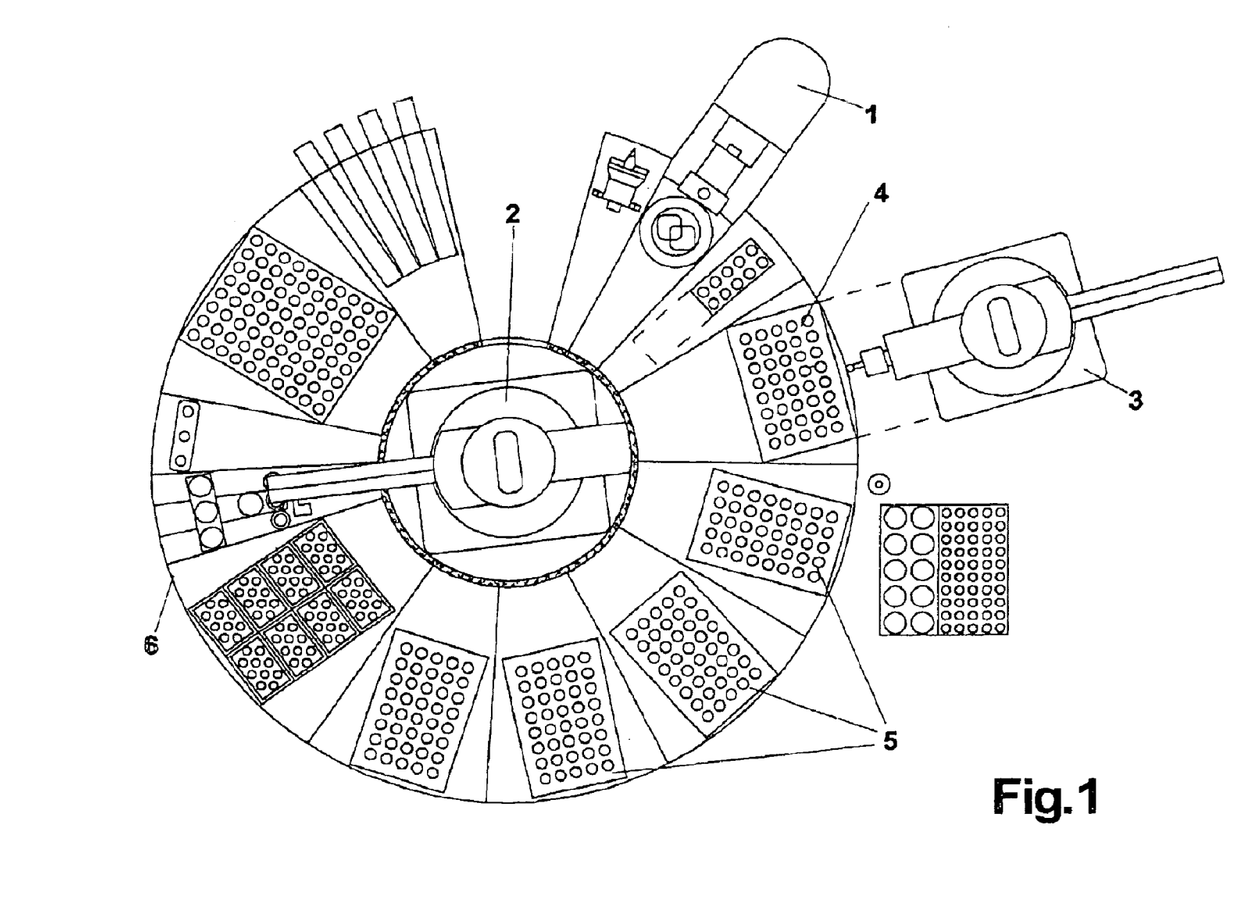
Figure 2:
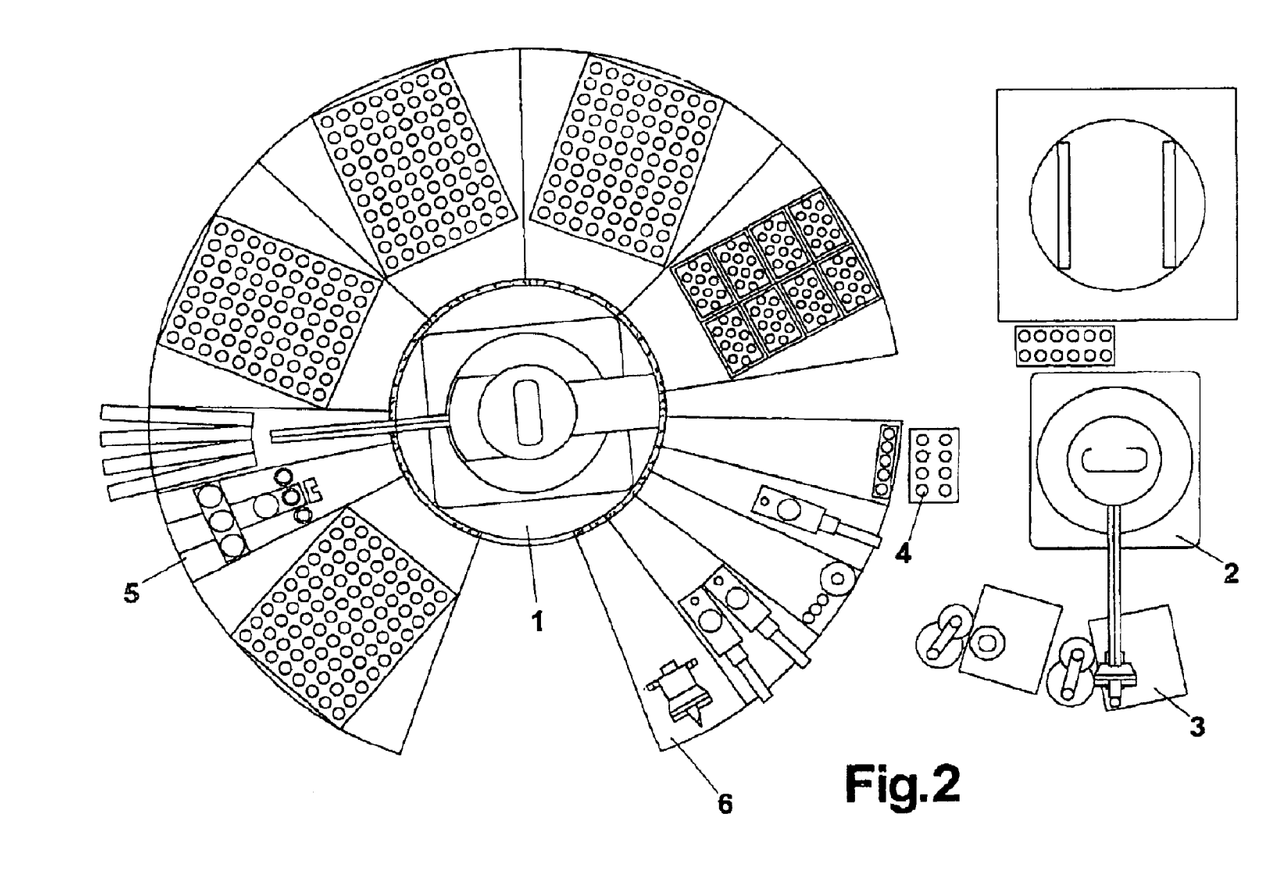

The substituted γ-lactone compounds according to the invention are preferably produced as described below on an automatic synthesis system from Zymark as shown in FIG. 1 and FIG. 2.

Instead of the above-described reaction of the reaction components of the general formulae II and III and glyoxalic acid in the presence of at least one organic and/or inorganic acid, these reaction components may also be reacted, optionally in the presence of at least one inorganic and/or organic acid, with microwave irradiation or with exposure to ultrasound.

The present invention accordingly also provides a process for the production of the γ-lactone compounds of the general formula I according to the invention, in which the residues $R^1$ to $R^4$ have the above-stated meaning, in accordance with which process at least one amine component of the above-stated general formula II, in which $R^1$ has the above-stated meaning, is reacted with glyoxalic acid, preferably in form of the monohydrate or an aqueous solution, and at least one alkene component of the above-stated general formula III, in which $R^2$ to $R^4$ have the above-stated meaning, in an organic solvent, optionally in the presence of at least one inorganic and/or organic acid with microwave irradiation or with exposure to ultrasound, preferably with microwave irradiation, to yield at least one compound of the above stated general formula I and this is optionally purified using conventional methods and/or optionally isolated using conventional methods.

The quantities of the reaction components to be used of the general formulae II and III and of the glyoxalic acid, the suitable temperature during the reaction and the suitable duration of the reaction may vary. The optimum quantity of the components to be used for the particular reaction, the optimum temperature and the optimum duration of the reaction may be determined by the person skilled in the art by simple preliminary testing. If the reaction proceeds with microwave irradiation, the temperature is preferably 40 to 70° C., particularly preferably 45 to 60° C. The duration of the reaction is preferably 0.1 to 60 minutes for microwave irradiation.

Acetonitrile or a mixture containing acetonitrile is preferably used as a suitable solvent.

The particular reaction components of the general formulae II and III and glyoxalic acid may be purchased commercially or be produced using conventional methods known to the person skilled in the art.

The substituted γ-lactone compounds of the general formula I according to the invention may be isolated as the free base or as the salt using the process according to the invention. The free base of the respective compound according to the invention of the general formula I may be converted into the corresponding physiologically acceptable salt using conventional methods known to the person skilled in the art, for example by reaction with an inorganic or organic acid, preferably with hydrochloric acid, hydrobromic acid, sulfuric acid, phosphoric acid, methanesulfonic acid, p-toluenesulfonic acid, carbonic acid, formic acid, acetic acid, oxalic acid, succinic acid, tartaric acid, mandelic acid, fumaric acid, lactic acid, citric acid, glutamic acid or aspartic acid. The free base may furthermore also be reacted with The free base of the respective compound of the general formula I according to the invention may also be converted into the corresponding physiologically acceptable salt with the free acid or a salt of a sugar substitute, such as for example saccharin, cyclamate or acesulfame.

Conversion of the free base of the respective compound according to the invention of the general formula I into the corresponding hydrochloride may preferably also be obtained by combining the compound of the general formula I according to the invention, dissolved in a suitable organic solvent, such as for example butan-2-one (methyl ethyl ketone), as a free base with trimethylsilyl chloride (TMSCl).

If the substituted γ-lactone compounds of the general formula I according to the invention are obtained by the production process according to the invention in the form of the racemates thereof or other mixtures of their various enantiomers and/or diastereomers, these may, if necessary, be separated and optionally isolated by conventional processes known to the person skilled in the art. Examples are chromatographic separation processes, in particular liquid chromatography processes at standard pressure or at elevated pressure, preferably MPLC and HPLC methods, and fractional crystallisation processes. Individual enantiomers, e.g. diastereomeric salts formed by means of HPLC on a chiral phase or by means of crystallisation with chiral acids, such as (+)-tartaric acid, (−)-tartaric acid or (+)-10-camphorsulfonic acid, may here in particular be separated from one another.

The γ-lactone compounds of the general formula I according to the invention are toxicologically safe and are therefore suitable as pharmaceutical active ingredients in pharmaceutical preparations.

The present invention accordingly also provides pharmaceutical preparations which contain at least one γ-lactone compound of the general formula I according to the invention, including the compounds excepted above, and optionally physiologically acceptable auxiliary substances.

The pharmaceutical preparations according to the invention are preferably suitable for combatting pain, particularly preferably for combatting chronic or neuropathic pain.

The pharmaceutical preparations according to the invention are likewise preferably suitable for the treatment or prevention of neurodegenerative diseases, in particular of Alzheimer's disease, Parkinson's disease or Huntington's chorea, or for the treatment or prevention of migraine, stroke, cerebral ischaemia, cerebral infarct, cerebral oedema, schizophrenia, psychoses brought about by elevated amino acid levels, AIDS dementia, Tourette's syndrome, inflammatory and/or allergic reactions, depression, mental health conditions, epilepsy, urinary incontinence, pruritus, tinnitus, diarrhoea, for anxiolysis or for anaesthesia.

The present invention accordingly also provides the use of at least one substituted γ-lactone compound of the general formula I, including the compounds excepted above, for the production a pharmaceutical preparation for combatting pain, in particular for combatting chronic or neuropathic pain, for the treatment or prevention of neurodegenerative diseases, in particular of Alzheimer's disease, Parkinson's disease or Huntington's chorea or for the treatment or prevention of migraine, stroke, cerebral ischaemia, cerebral infarct, cerebral oedema, schizophrenia, psychoses brought about by elevated amino acid levels, AIDS dementia, Tourette's syndrome, inflammatory and/or allergic reactions, depression, mental health conditions, epilepsy, urinary incontinence, pruritus, tinnitus, diarrhoea, for anxiolysis or anaesthesia.

The pharmaceutical preparations according to the invention may also contain mixtures of various stereoisomers of one or more γ-lactone compounds according to the invention. Various enantiomers of a γ-lactone compound according to the invention may accordingly, for example, also be present in non-equimolar quantities.

In addition to at least one substituted γ-lactone compound according to the invention, the pharmaceutical preparations according to the invention conventionally contain further physiologically acceptable auxiliary substances, which are preferably selected from the group consisting of matrix materials, fillers, solvents, diluents, dyes and binders. The pharmaceutical preparations according to the invention may be present as liquid, semisolid or solid dosage forms, for example in the form of solutions for injection, drops, succi, syrups, sprays, suspensions, tablets, patches, capsules, transdermal delivery systems, suppositories, ointments, creams, lotions, gels, emulsions, aerosols or in multiparticulate form, for example in the form of pellets or granules, and also be administered as such.

Selection of the physiologically acceptable auxiliary substances and the quantities thereof which are to be used depends upon whether the pharmaceutical preparation is to be administered orally, perorally, parenterally, intravenously, intraperitoneally, intradermally, intramuscularly, intranasally, buccally, rectally or topically, for example onto infections of the skin, mucous membranes or eyes. Preparations in the form of tablets, coated tablets, capsules, granules, drops, succi and syrups are suitable for oral administration, while solutions, suspensions, easily reconstitutible dried preparations and sprays are suitable for parenteral, topical and inhalatory administration. Substituted γ-lactone derivatives according to the invention in a depot in dissolved form or in a dressing, optionally with the addition of skin penetration promoters, are suitable percutaneous administration preparations. Orally or percutaneously administrable formulations may release the substituted γ-lactone derivatives according to the invention in delayed manner.

Production of the pharmaceutical preparations according to the invention proceeds with the assistance of conventional means, devices, methods and processes known to the person skilled in the art, such as are described for example in "Remington's Pharmaceutical Sciences", ed. A. R. Gennaro, 17th ed., Mack Publishing Company, Easton, Pa. (1985), in particular in part 8, chapters 76 to 93. The corresponding literature description is hereby introduced as a reference and is deemed to be part of the disclosure.

The quantity of the respective compound of the general formula I according to the invention to be administered to the patient may vary and is for example dependent on the weight or age of the patient and on the mode of administration, the indication and the severity of the complaint. 0.5 to 500 mg per kg patient body weight of at least one compound of the general formula I according to the invention are conventionally administered.

Molecular Pharmacological Investigations:

The investigations for determining the affinity of the γ-lactone compounds of the general formula I according to the invention for the glycine-binding site of the NMDA receptor channel were performed on brain membrane homogenates (homogenate of cortex and hippocampus area from the brain of male rats, Wistar strain, Charles River, WIGA GmbH, Sulzbach, Germany), as described in B. M. Baron et al., Journal of Pharmacology and Experimental Therapeutics, vol. 279, pages 62–68, 1996. The corresponding literature description is hereby introduced as a reference and is deemed to be part of the disclosure.

To this end, the cortex and hippocampus were dissected out of freshly harvested rat brains and homogenised with ice cooling in 5 mmol/l of TRIS-acetate buffer, 0.32 mol/l of sucrose, pH 7.4 (10 ml/g fresh weight) using a Potter homogeniser (Braun, Melsungen, Germany, 10 piston strokes at 500 revolutions per minute (rpm)) and then centrifuged for 10 minutes at 1,000 g and 4° C. The first supernatant was collected and the sediment again homogenised with ice cooling with 5 mmol/l of TRIS-acetate buffer, 0,32 mol/l of sucrose, pH 7.4 (5 ml/g of original fresh weight of rat cerebral cortex and hippocampus) with the Potter homogeniser (10 piston strokes at 500 rpm) and centrifuged for 10 minutes at 1,000 g and 4° C. The resultant supernatant was combined with the supernatant from the first centrifugation and centrifuged at 17,000 g for 20 minutes at 4° C. The supernatant after this centrifugation was discarded and the membrane sediment was resuspended with 5 mmol/l of TRIS-acetate buffer, pH 8.0 (20 ml/g of original fresh weight) and homogenised with 10 piston strokes at 500 rpm.

The membrane homogenate was then incubated for 1 hour at 4° C. and centrifuged for 30 minutes at 50,000 g and 4° C. The supernatant was discarded and the centrifuge tubes containing the membrane sediment were sealed with Parafilm and frozen for 24 hours at −20° C. On the following day, the membrane sediment was thawed and resuspended with ice-cold 5 mmol/l TRIS-acetate buffer, 0,1% saponin (wt./vol.), pH 7.0 (10 ml/g of original fresh weight) and homogenised with 10 piston strokes at 500 rpm and then centrifuged for 20 minutes at 50,000 g and 4° C. The resultant supernatant was discarded and the sediment resuspended in a small volume with 5 mmol/l of TRIS-acetate buffer, pH 7.0 (approx. 2 ml/g of original fresh weight) and again homogenised with 10 piston strokes at 500 rpm. After determination of the protein content, the membrane homogenate was adjusted with 5 mmol/l TRIS-acetate buffer, pH 7.0, to a protein concentration of 10 mg of protein/ml and frozen in aliquots until used for testing.

The receptor binding test was performed by thawing aliquots, diluting them 1:10 with 5 mmol/l TRIS-acetate buffer, pH 7.0, homogenising them with ice-cooling with 10 piston strokes at 500 rpm with the Potter homogeniser and centrifuging them for 60 minutes at 55,000 g at 4° C. The supernatant was decanted and the membrane sediment adjusted with ice-cold 50 mmol/l TRIS-acetate buffer, pH 7.0, to a protein concentration of 1 mg/ml and again homogenised with 10 piston strokes at 500 rpm and kept in suspension in an ice bath with stirring on a magnetic stirrer. This membrane homogenate was used in the receptor binding test in a quantity of 100 µl per 1 ml batch (0.1 mg of protein/ml in the final batch).

In the binding test, 50 mmol/l TRIS-acetate buffer pH 7.0 was used as the buffer and 1 nmol/l of ($^3$H)-MDL 105.519 was used as the radioactive ligand, as described in the above-stated literature reference by B. M. Baron et al. The level of non-specific binding was determined in the presence of 1 mmol/l of glycine.

In further batches, the compounds of the general formula I according to the invention were added in concentration series and the displacement of the radioactive ligand from its specific binding at the glycine-binding site of the NMDA receptor channel was determined. Each of the triplicate batches was incubated for 120 minutes at 4° C. and then harvested by filtration through glass fibre filter mats (Whatman, type GF/B, Adi Hassel, Munich, Germany) in order to determine the radioactive ligand bound to the membrane homogenate. The radioactivity retained on the glass fibre filters was measured, after addition of scintillating material (Ready Protein, Beckmann Coulter GmbH, Krefeld, Germany) in the β-counter (Packard TRI-CARB Liquid Scintillation Analyzer 2000CA, Packard Instrument, Meriden, Conn. 06450, USA).

The affinity of the compounds of the general formula I according to the invention for the glycine-binding site of the NMDA receptor channel was calculated as an $IC_{50}$ value (concentration with 50% displacement of the radioactive ligand from its specific bond) in accordance with the mass-action law by means of nonlinear regression and, after conversion using the Cheng-Prusoff equation, described in Y. Cheng, W. H. Prusoff, 1973, Biochem. Pharmacol., vol. 22, pages 3099–3108, is stated as a Ki value.

The present invention is explained below with reference to Examples. These explanations are given merely by way of example and do not restrict the general concept of the invention.

EXAMPLES

The chemicals and solvents used for the production of γ-lactone compounds according to the invention were purchased commercially, for example from Acros, Avocado, Aldrich, Fluka, Lancaster, Maybridge, Merck, Sigma or TCI, or produced using conventional methods known to the person skilled in the art.

Thin-layer chromatography was performed with pre-coated silica gel 60 F 254 HPTLC plates from E. Merck, Darmstadt.

The yields of the compounds produced have not been optimised.

Analysis was performed by ESI mass spectroscopy or NMR spectroscopy.

General Procedure 1:

The γ-lactone compounds according to the invention were synthesised on an automatic synthesis system from Zymark as shown in FIG. 1 and FIG. 2.

FIG. 1 shows a capper station (ref. numeral 1) for closing the reaction microtubes, a robot 1 (ref. numeral 2) and a robot 2 (ref. numeral 3), wherein the robot 1 moves the reaction microtubes or the corresponding racks and robot 2 pipettes the reagents into the reaction microtubes, a temperature-controllable reactor block (ref. numeral 4), stirring blocks (ref. numeral 5) and a filtration station (ref. numeral 6), in which the reaction solution is filtered off.

FIG. 2 likewise shows a robot 1 (ref. numeral 1) and a robot 2 (ref. numeral 2), both of which move the glass microtubes holding the synthesis products to the various stations. In detail, the stations comprise a vortexer (ref. numeral 3) for mixing the samples and for apportioning solutions or solvents, a spin reactor (ref. numeral 4) for mixing samples, a phase detection station (ref. numeral 5) for detecting the phase boundary and phase separation and a station (ref. numeral 6) for drying the synthesis products by means of salt cartridges.

For the purposes of synthesis, a round-bottomed glass microtube (diameter 16 mm, length 125 mm) with thread was provided manually with a stirrer and closed on the capper station (ref. numeral 1) according to FIG. 1 with a screw cap with septum. The tube was placed by robot 1 (ref. numeral 2) in the reactor block (ref. numeral 4), which was temperature-controlled to 20° C. Robot 2 (ref. numeral 3) pipetted in the following reagents in succession:
1.) 1 ml of a solution of trifluoroacetic acid and the particular amine component, in each case 0.1 M in acetonitrile,
2.) 1 ml of a 0.11 M glyoxalic acid monohydrate solution in acetonitrile
3.) 1 ml of a 0.3 M solution of the particular alkene component in acetonitrile The reaction mixture was then stirred at 20° C. in one of the stirring blocks (ref. numeral 5) for 600 minutes. The reaction solution was then filtered off in the filtration station (ref. numeral 6). The tube was here rinsed twice with 1.5 ml portions of a 7.5 wt. % sodium hydrogencarbonate solution.

The rack holding the tubes was then placed manually onto an automatic working up unit according to FIG. 2, where the reaction mixture was combined and shaken with 2 ml of diethyl ether on a vortexer (ref. numeral 3).

Thorough mixing was then performed for ten minutes in the spin reactor (ref. numeral 4) and a distinct phase boundary was formed by slowly decreasing the rotary motion. This phase boundary was detected optically on the phase detection station (ref. numeral 5) and the organic phase was removed by pipette. In the next step, the aqueous phase was again combined with 2 ml of diethyl ether, shaken, centrifuged and the organic phase removed by pipette. The combined organic phases were dried over 2.4 g of $MgSO_4$ (pellets). The solvent was removed in a vacuum centrifuge. Each sample was then analysed by electron spray ionisation mass spectrometry (ESI-MS) and/or NMR spectroscopy.

Automated synthesis ensures identical treatment for all samples and consistent reaction control. The γ-lactone compounds according to the examples and produced in accordance with the above general procedure are listed in Table 1 below:

TABLE 1

| Example | Name | Calculated mass | Actual mass (ESI) |
|---|---|---|---|
| 1 | 3-(2-Chloro-4-fluoro-phenylamino)-5-(4-fluoro-phenyl)-5-methyl-dihydro-furan-2-one | 337.75 | 338.1 |
| 2 | 5-Methyl-3-(4-phenoxy-phenylamino)-5-phenyl-dihydro-furan-2-one | 359.42 | 360.1 |
| 3 | 3-(2-Chloro-phenylamino)-5-(4-fluoro-phenyl)-5-methyl-dihydro-furan-2-one | 319.76 | 320.2 |
| 4 | 3-(4-Chloro-2-methyl-phenylamino)-5-methyl-5-phenyl-dihydro-furan-2-one | 315.8 | 316.1 |
| 5 | 3-(2,4-Dichloro-phenylamino)-5-(4-fluoro-phenyl)-5-methyl-dihydro-furan-2-one | 354.21 | 354.2/ 356.1 |
| 6 | 3-(4-Chloro-3-trifluoromethyl-phenylamino)-5-methyl-5-phenyl-dihydro-furan-2-one | 369.77 | 370.1/ 372.1 |
| 7 | 3-(2,3-Dichloro-phenylamino)-5-(4-fluoro-phenyl)-5-methyl-dihydro-furan-2-one | 354.21 | 354.1/ 356.1 |
| 8 | 3-(4-Iodo-phenylamino)-5-methyl-5-phenyl-dihydro-furan-2-one | 393.22 | 394.0 |
| 9 | 3-(4-Chloro-2-fluoro-phenylamino)-5-(4-fluoro-phenyl)-5-methyl-dihydro-furan-2-one | 337.75 | 338.1 |
| 10 | 3-(2-Chloro-4-methyl-phenylamino)-5-methyl-5-phenyl-dihydro-furan-2-one | 315.8 | 316.2 |
| 11 | 3-(2-Chloro-4-methyl-phenylamino)-5-(4-fluoro-phenyl)-5-methyl-dihydro-furan-2-one | 333.79 | 334.2 |
| 12 | 3-(3,5-Dichloro-phenylamino)-5-methyl-5-phenyl-dihydro-furan-2-one | 336.22 | 336.1/ 338.0 |
| 13 | 3-(3,5-Dichloro-phenylamino)-5-(4-fluoro-phenyl)-5-methyl-dihydro-furan-2-one | 354.21 | 354.0 |
| 14 | 3-(4-Bromo-2-chloro-phenylamino)-5-(4-fluoro-phenyl)-5-methyl-dihydro-furan-2-one | 398.66 | 398.1/ 400.0 |
| 15 | 4-(5-Methyl-2-oxo-5-phenyl-tetrahydro-furan-3-ylamino)-benzonitrile | 292.34 | 293.3 |
| 16 | 5-(4-Chloro-phenyl)-3-(4-iodo-phenylamino)-5-methyl-dihydro-furan-2-one | 427.67 | 428.0 |
| 17 | 5-(4-Chloro-phenyl)-3-(2,4-dichloro-phenylamino)-5-methyl-dihydro-furan-2-one | 370.66 | 370.1/ 372.1 |
| 18 | 5-(4-Chloro-phenyl)-3-(2-chloro-phenylamino)-5-methyl-dihydro-furan-2-one | 336.22 | 336.2/ 338.0 |
| 19 | 3-(4-Chloro-2-methyl-phenylamino)-5-(4-chloro-phenyl)-5-methyl-dihydro-furan-2-one | 350.24 | 350.2/ 352.0 |
| 20 | 3-(2-Chloro-4-fluoro-phenylamino)-5-(4-chloro-phenyl)-5-methyl-dihydro-furan-2-one | 354.21 | 354.1/ 356.1 |
| 21 | 3-(4-Chloro-2-fluoro-phenylamino)-5-(4-chloro-phenyl)-5-methyl-dihydro-furan-2-one | 354.21 | 354.1/ 356.1 |
| 22 | 3-(2-Chloro-4-methyl-phenylamino)-5-(4-chloro-phenyl)-5-methyl-dihydro-furan-2-one | 350.24 | 350.1/ 352.0 |
| 23 | 5-(4-Chloro-phenyl)-3-(2,3-dichloro-phenylamino)-5-methyl-dihydro-furan-2-one | 370.66 | 370.1/ 372.1 |
| 24 | 3-(4-Bromo-2-chloro-phenylamino)-5-(4-chloro-phenyl)-5-methyl-dihydro-furan-2-one | 415.12 | 414.1/ 416.0/ 418.0 |
| 25 | 5-(4-Chloro-phenyl)-3-(3,5-dichloro-phenylamino)-5-methyl-dihydro-furan-2-one | 370.66 | 370.1/ 372.0 |
| 26 | 3-(3,5-Dibromo-pyridin-2-ylamino)-5-methyl-5-phenyl-dihydro-furan-2-one | 426.12 | 427.1 |
| 27 | 5-(4-Chloro-phenyl)-3-(3,5-dichloro-pyridin-2-ylamino)-5-methyl-dihydro-furan-2-one | 371.65 | 371.0/ 373.0 |
| 28 | 5-(4-Chloro-phenyl)-5-methyl-3-(5-nitro-pyridin-2-ylamino)-dihydro-furan-2-one | 347.76 | 348.1 |
| 29 | 3-(3-Chloro-2-methyl-phenylamino)-5-(4-iodo-phenyl)-5-methyl-dihydro-furan-2-one | 441.69 | 442.0 |
| 30 | 5-(4-Bromo-phenyl)-3-(4-chloro-phenylamino)-5-methyl-dihydro-furan-2-one | 380.67 | 380.1/ 382.1 |
| 31 | 5-(3-Chloro-phenyl)-3-(4-chloro-phenylamino)-5-methyl-dihydro-furan-2-one | 336.21 | 336.1/ 338.1 |
| 32 | 3-(4-Chloro-phenylamino)-5-(4-iodo-phenyl)-5-methyl-dihydro-furan-2-one | 427.66 | 428.0 |
| 33 | 5-(4-Bromo-phenyl)-3-(2-iodo-phenylamino)-5-methyl-dihydro-furan-2-one | 472.12 | 472.0/ 474.0 |
| 34 | 5-(3-Chloro-phenyl)-3-(2-iodo-phenylamino)-5-methyl-dihydro-furan-2-one | 427.66 | 428.1 |
| 35 | 5-(4-Iodo-phenyl)-3-(2-iodo-phenylamino)-5-methyl-dihydro-furan-2-one | 519.11 | 519.9 |
| 36 | 3-(2,4-Difluoro-phenylamino)-5-methyl-5-naphthalen-1-yl-dihydro-furan-2-one | 353.36 | 354.0 |
| 37 | 5-(4-Bromo-phenyl)-3-(4-Iodo-phenylamino)-5-methyl-dihydro-furan-2-one | 472.12 | 472.0 |
| 38 | 5-(3-Chloro-phenyl)-3-(4-iodo-phenylamino)-5-methyl-dihydro-furan-2-one | 427.66 | 428.0 |

TABLE 1-continued

| Example | Name | Calculated mass | Actual mass (ESI) |
|---|---|---|---|
| 39 | 3-(4-Iodo-phenylamino)-5-methyl-5-naphthalen-1-yl-dihydro-furan-2-one | 443.28 | 444.0 |
| 40 | 5-(4-Bromo-phenyl)-3-(3,5-dichloro-phenylamino)-5-methyl-dihydro-furan-2-one | 415.11 | 414.0/ 416.0 |
| 41 | 5-(3-Chloro-phenyl)-3-(3,5-dichloro-phenylamino)-5-methyl-dihydro-furan-2-one | 370.66 | 370.0/ 372.0 |
| 42 | 3-(3,5-Dichloro-phenylamino)-5-(4-iodo-phenyl)-5-methyl-dihydro-furan-2-one | 462.11 | 461.9/ 463.9 |
| 43 | 3-(3,5-Dichloro-phenylamino)-5-methyl-5-naphthalen-1-yl-dihydro-furan-2-one | 386.27 | 386.0/ 387.9 |
| 44 | 5-(3-Chloro-phenyl)-5-methyl-3-phenylamino-dihydro-furan-2-one | 301.77 | 302.1 |
| 45 | 3-(2-Bromo-4-methyl-phenylamino)-5-(4-iodo-phenyl)-5-methyl-dihydro-furan-2-one | 486.15 | 485.9/ 487.9 |
| 46 | 3-(2-Bromo-4-methyl-phenylamino)-5-methyl-5-naphthalen-1-yl-dihydro-furan-2-one | 410.31 | 410.0/ 412.0 |
| 47 | 3-(5-Chloro-2-methyl-phenylamino)-5-methyl-5-(5,6,7,8-tetrahydro-naphthalen-2-yl)-dihydro-furan-2-one | 369.89 | 370.1 |
| 48 | 3-(4-Bromo-2-fluoro-phenylamino)-5-isopropyl-5-phenyl-dihydro-furan-2-one | 392.27 | 392.1/ 394.1 |
| 49 | 5-(2,5-Dimethoxy-phenyl)-5-methyl-3-(5-trifluoromethyl-pyridin-2-ylamino)-dihydro-furan-2-one | 396.36 | 397.2 |
| 50 | 5-(3,5-Dimethoxy-phenyl)-5-methyl-3-(5-trifluoromethyl-pyridin-2-ylamino)-dihydro-furan-2-one | 396.36 | 397.1 |
| 51 | 3-(3-Bromo-5-methyl-pyridin-2-ylamino)-5-(2-methoxy-phenyl)-5-methyl-dihydro-furan-2-one | 391.26 | 391.1/ 393.1 |
| 52 | 3-(3-Bromo-5-methyl-pyridin-2-ylamino)-5-(2,5-dimethoxy-phenyl)-5-methyl-dihydro-furan-2-one | 421.29 | 421.1 |
| 53 | 3-(3-Bromo-5-methyl-pyridin-2-ylamino)-5-(3,5-dimethoxy-phenyl)-5-methyl-dihydro-furan-2-one | 421.29 | 421.1 |
| 54 | 3-(5-Bromo-3-methyl-pyridin-2-ylamino)-5-(2-methoxy-phenyl)-5-methyl-dihydro-furan-2-one | 391.26 | 391.2/ 393.1 |
| 55 | 3-(2-Chloro-pyridin-3-ylamino)-5-(2-methoxy-phenyl)-5-methyl-dihydro-furan-2-one | 332.78 | 333.3 |
| 56 | 3-(5-Bromo-pyridin-2-ylamino)-5-(2,5-dimethoxy-phenyl)-5-methyl-dihydro-furan-2-one | 407.26 | 407.1/ 409.1 |
| 57 | 3-(3-Chloro-5-trifluoromethyl-pyridin-2-ylamino)-5-(2,5-dimethoxy-phenyl)-5-methyl-dihydro-furan-2-one | 430.8 | 431.1 |
| 58 | 5-(2-Methoxy-phenyl)-5-methyl-3-(pyridin-2-ylamino)-dihydro-furan-2-one | 298.34 | 299.2 |
| 59 | 3-[5-(2,5-Dimethoxy-phenyl)-5-methyl-2-oxo-tetrahydro-furan-3-ylamino]-pyrazole-4-carboxylic acid ethyl ester | 389.4 | 390.2 |
| 60 | 3-[5-(3-Bromo-phenyl)-5-methyl-2-oxo-tetrahydro-furan-3-ylamino]-pyrazole-4-carboxylic acid ethyl ester | 408.25 | 408.1 |
| 61 | 3-[5-(3-Bromo-phenyl)-5-methyl-2-oxo-tetrahydro-furan-3-ylamino]-5-methylsulfanyl-pyrazole-4-carbonitrile | 407.29 | 407.1/ 409.0 |
| 62 | 3-[5-(2,5-Dimethoxy-phenyl)-5-methyl-2-oxo-tetrahydro-furan-3-ylamino]-pyrazole-4-carbonitrile | 342.35 | 343.1 |
| 63 | 3-(4-Bromo-pyrazol-3-ylamino)-5-(3,5-dimethoxy-phenyl)-5-methyl-dihydro-furan-2-one | 396.24 | 396.1/ 398.1 |
| 64 | 3-(4-Bromo-5-phenyl-2H-pyrazol-3-ylamino)-5-(2-methoxy-phenyl)-5-methyl-dihydro-furan-2-one | 442.31 | 442.1/ 444.1 |
| 65 | 3-(8-Hydroxy-quinolin-2-ylamino)-5-(2-methoxy-phenyl)-5-methyl-dihydro-furan-2-one | 364.4 | 365.2 |
| 66 | 5-(2,5-Dimethoxy-phenyl)-3-(8-hydroxy-quinolin-2-ylamino)-5-methyl-dihydro-furan-2-one | 394.42 | 395.2 |
| 67 | 5-(2-Methoxy-phenyl)-5-methyl-3-(pyrazin-2-ylamino)-dihydro-furan-2-one | 299.32 | 300.2 |
| 68 | 5-(3-Bromo-phenyl)-5-methyl-3-(4-methyl-pyrimidin-2-ylamino)-dihydro-furan-2-one | 362.23 | 362.1/ 364.1 |
| 69 | 2-[5-(3,5-Dimethoxy-phenyl)-5-methyl-2-oxo-tetrahydro-furan-3-ylamino]-4-propyl-pyrimidine-5-carboxylic acid ethyl ester | 443.49 | 444.1 |
| 70 | 5-(2-Methoxy-phenyl)-5-methyl-3-(pyrimidin-2-ylamino)-dihydro-furan-2-one | 299.32 | 300.2 |
| 71 | 3-(4-Chloro-3-trifluoromethyl-phenylamino)-5-phenyl-5-propyl-dihydro-furan-2-one | 397.82 | 398.0 |
| 72 | 3-(2-Chloro-phenylamino)-5-phenyl-5-propyl-dihydro-furan-2-one | 329.82 | 330.1 |
| 73 | 3-(2-Chloro-4-fluoro-phenylamino)-5-phenyl-5-propyl-dihydro-furan-2-one | 347.81 | 348.1 |
| 74 | 3-(4-Chloro-2-fluoro-phenylamino)-5-phenyl-5-propyl-dihydro-furan-2-one | 347.81 | 348.1 |
| 75 | 3-(2-Chloro-4-methyl-phenylamino)-5-phenyl-5-propyl-dihydro-furan-2-one | 343.85 | 344.1 |
| 76 | 3-(2-Oxo-5-phenyl-5-propyl-tetrahydro-furan-3-ylamino)-pyrazole-4-carboxylic acid ethyl ester | 357.4 | 358.1 |
| 77 | 3-(5-Hydroxy-4-phenylazo-pyrazol-3-ylamino)-5-phenyl-5-propyl-dihydro-furan-2-one | 405.45 | 406.2 |
| 78 | 3-(4-Bromo-5-phenyl-pyrazol-3-ylamino)-5-phenyl-5-propyl-dihydro-furan-2-one | 440.34 | 440.1/ 442.1 |
| 79 | 5-Methylsulfanyl-3-(2-oxo-5-phenyl-5-propyl-tetrahydro-furan-3-ylamino)-pyrazole-4-carbonitrile | 356.44 | 357.1 |
| 80 | 3-(5-Butyl-2-oxo-5-phenyl-tetrahydro-furan-3-ylamino)-pyrazole-4-carboxylic acid ethyl ester | 371.43 | 372.1 |
| 81 | 5-Butyl-3-(5-hydroxy-4-phenylazo-pyrazol-3-ylamino)-5-phenyl-dihydro-furan-2-one | 419.48 | 420.2 |
| 82 | 3-(4-Bromo-5-phenyl-pyrazol-3-ylamino)-5-butyl-5-phenyl-dihydro-furan-2-one | 454.37 | 454.1 |
| 83 | 3-(5-Butyl-2-oxo-5-phenyl-tetrahydro-furan-3-ylamino)-5-methylsulfanyl-pyrazole-4-carbonitrile | 370.47 | 371.1 |
| 84 | 3-(5-butyl-2-oxo-5-phenyl-tetrahydro-furan-3-ylamino)-pyrazole-4-carbonitrile | 324.38 | 325.1 |
| 85 | 5-Butyl-3-(2-phenoxy-phenylamino)-5-phenyl-dihydro-furan-2-one | 401.5 | 402.1 |
| 86 | 5-Biphenyl-4-yl-3-(2,4-dichloro-phenylamino)-5-methyl-dihydro-furan-2-one | 412.31 | 412.0/ 414.0 |
| 87 | 5-Biphenyl-4-yl-3-(2-chloro-phenylamino)-5-methyl-dihydro-furan-2-one | 377.87 | 378.1 |
| 88 | 5-Biphenyl-4-yl-3-(2-chloro-4-fluoro-phenylamino)-5-methyl-dihydro-furan-2-one | 395.86 | 396.1 |
| 89 | 3-(5-Biphenyl-4-yl-5-methyl-2-oxo-tetrahydro-furan-3-ylamino)-pyrazole-4-carboxylic acid ethyl ester | 405.45 | 406.1 |
| 90 | 5-Biphenyl-4-yl-3-(4-bromo-5-phenyl-pyrazol-3-ylamino)-5-methyl-dihydro-furan-2-one | 488.38 | 490.1 |

General Procedure 2:

1 mol equivalent of the respective amine component and 1.5 mol equivalents of glyoxylic acid monohydrate were dissolved with stirring at room temperature in 10 ml of acetonitrile, combined with 1 mol equivalent of trifluoroacetic acid and then with 1.5 to 3 mol equivalents of the respective alkene component. The course of the reaction was monitored by thin-layer chromatography (mobile solvent system diethyl ether/hexane, 1:1) and is complete after two to twelve hours (TLC verification). The reaction batch was combined with an excess of saturated, aqueous sodium hydrogencarbonate solution and the aqueous phase was extracted three times with diethyl ether. The organic phase was washed to neutrality with water, dried over magnesium sulfate, filtered out, washed with diethyl ether and evaporated. The products were isolated by precipitation as the hydrochloride directly or after silica gel chromatography (silica gel 60) with ether/diisopropyl ether or ether/hexane mixtures of variable composition.

The isolated products were characterised by $^1$H-NMR spectroscopy and ESI mass spectrometry.

The γ-lactone compounds produced according to general procedure 2 are shown in Table 2 below:

TABLE 2

| Example | Name |
|---|---|
| 91 | 3-(3,5-Dichlorophenylamino)-5-methyl-5-phenyl-dihydrofuran-2-one hydrochloride |
| 92 | 3-(3,5-Dichlorophenylamino)-5-methyl-5-o-tolyl-dihydrofuran-2-one |
| 93 | 3-(3,5-Dichlorophenylamino)-5-(4-fluorophenyl)-5-methyl-dihydrofuran-2-one hydrochloride |
| 94 | 5-(2-Chlorophenyl)-3-(3,5-dichlorophenylamino)-5-methyl-dihydrofuran-2-one |
| 95 | 5-(4-Chlorophenyl)-3-(3,5-dichlorophenylamino)-5-methyl-dihydrofuran-2-one |
| 96 | 5-(3-Bromophenyl)-3-(3,5-dichlorophenylamino)-5-methyl-dihydrofuran-2-one hydrochloride |
| 97 | 5-(4-Bromophenyl)-3-(3,5-dichlorophenylamino)-5-methyl-dihydrofuran-2-one hydrochloride |
| 98 | 3-(3,5-Dichlorophenylamino)-5-(4-iodophenyl)-5-methyl-dihydrofuran-2-one hydrochloride |
| 99 | 3-(3,5-Dichlorophenylamino)-5-(2-methoxyphenyl)-5-methyl-dihydrofuran-2-one |
| 100 | 3-(3,5-dichlorophenylamino)-5-(3-methoxyphenyl)-5-methyl-dihydrofuran-2-one hydrochloride |
| 101 | 3-(3,5-Dichlorophenylamino)-5-(4-methoxyphenyl)-5-methyl-dihydrofuran-2-one |
| 102 | 3-(3,5-Dichlorophenylamino)-5-(2,4-dimethoxyphenyl)-5-methyl-dihydrofuran-2-one |
| 103 | 3-(3,5-Dichlorophenylamino)-5-(2,5-dimethoxyphenyl)-5-methyl-dihydrofuran-2-one |
| 104 | 3-(3,5-Dichlorophenylamino)-5-(3,5-dimethoxyphenyl)-5-methyl-dihydrofuran-2-one |
| 105 | 5-(Biphenyl-4-yl-)3-(3,5-dichlorophenylamino)-5-methyl-dihydrofuran-2-one |
| 106 | 3-(3,5-Dichlorophenylamino)-5-ethyl-5-phenyl-dihydrofuran-2-one |
| 107 | 3-(3,5-Dichlorophenylamino)-5-phenyl-5-n-propyl-dihydrofuran-2-one |
| 108 | 5-n-Butyl-3-(3,5-dichlorophenylamino)-5-phenyl-dihydrofuran-2-one |
| 109 | 3-(3,5-Dichlorophenylamino)-7a-phenyl-hexahydrobenzofuran |
| 110 | 3-(3,5-Dichlorophenylamino)-7a-(3-methoxy-phenyl)-hexahydrobenzofuran-2-one |
| 111 | 3-(3,5-Dichlorophenylamino)-8a-(3-methoxy-phenyl)-octahydrocyclohepta[b]furan-2-one |

General Procedure 3:

The reactions with microwave irradiation were performed in a laboratory microwave oven, model MLS ETHOS 600 from MLS-GmbH (D-88299 Leutkirch, Auenweg 37, Germany).

For the purposes of synthesis, 1 mol equivalent of the respective amino component, 1.5 mol equivalents of glyoxalic acid monohydrate and 1.5 to 3 mol equivalents of the respective alkene component in acetonitrile were introduced into a pressure-resistant Teflon vessel, which was closed with a Teflon lid and in held in a safety clamp to discharge excess pressure. The reaction temperature was monitored in a second Teflon vessel, which likewise contained acetonitrile. The reaction temperature was monitored and adjusted by an external control computer via an internal fibre optic cable which passed through a quartz tube into the second Teflon vessel.

The reaction mixture was heated in the microwave oven within one minute to 55° C. and left at this temperature for five minutes. After cooling, the vessel placed in ice water, cautiously opened and evaporated in a rotary evaporator. A dark brown oil was obtained. The crude products obtained in this manner were purified by silica gel chromatography (silica gel 60) with ether/diisopropyl ether or ether/hexane mixtures of variable composition and were then isolated as hydrochlorides by precipitation.

The isolated products were characterised by $^1$H-NMR spectroscopy and ESI mass spectrometry.

Pharmacological Investigations

Receptor Binding Investigations

The investigations for determining the affinity of the compounds according to the invention according to Examples 12, 13, 25 and 108 for the glycine-binding site of the NMDA receptor channel were performed as described above.

The glycine-binding site affinity of the NMDA receptor channel was calculated as an $IC_{50}$ value (concentration with 50% displacement of the radioactive ligand from its specific bond) in accordance with the mass-action law by means of nonlinear regression and, after conversion (using the Cheng-Prusoff equation (Y. Cheng, W. H. Prusoff, 1973, Biochem. Pharmacol., vol. 22, pages 3099–3108)), is stated in Table 3 below as a Ki value.

TABLE 3

| | Glycine-binding site of the NMDA receptor channel | |
|---|---|---|
| Example | Ki (µM) | % inhibition (10 µM) |
| 12 | 0.8 | 80 |
| 13 | 0.8 | 70 |
| 25 | 1.3 | 71 |
| 108 | not determined | 62 |

What is claimed is:

1. Substituted γ-lactone compounds of the general formula I, in which $R^1$ denotes an optionally at least mono-substituted aryl or heteroaryl residue, an optionally at least mono-substituted aryl or heteroaryl residue attached via a $C_{1-6}$ alkylene group, an optionally at least mono-substituted, saturated, branched or unbranched aliphatic $C_{1-10}$ residue, an optionally at least mono-substituted, at least partially unsaturated, branched or unbranched aliphatic $C_{2-10}$ residue or an optionally at least mono-substituted, saturated or at least mono-unsaturated cycloaliphatic $C_{3-9}$ residue, $R^2$ denotes an optionally at least mono-substituted, saturated, branched or unbranched aliphatic $C_{1-10}$ residue or an optionally at least mono-substituted, at least partially unsaturated, branched or unbranched aliphatic $C_{2-10}$ residue, $R^3$ denotes an optionally at least mono-substituted aryl residue, $R^4$ denotes H, or $R^3$ and $R^4$ together denote an optionally at least mono-substituted, saturated or at least mono-unsaturated aliphatic $C_{3-7}$ residue, with the proviso that the residue $R^2$ in this case denotes an optionally at least mono-substituted aryl residue, an optionally at least mono-substituted, saturated, branched or unbranched aliphatic $C_{1-10}$ residue or an optionally at least mono-substituted, at least partially unsaturated, branched or unbranched aliphatic $C_{2-10}$ residue in the form of the racemates, diastereomers or enantiomers thereof in the form of the base thereof or of a corresponding physiologically acceptable salt, wherein the compounds of the general formula I, in which $R^1$ denotes a 2-, 4-, 6-trichlorophenyl residue, $R^2$ a methyl residue, $R^3$ a phenyl residue and $R^4$ denotes H, are excepted.

2. Substituted γ-lactone compounds according to claim 1, characterised in that $R^1$ denotes an optionally at least mono-substituted aryl or heteroaryl residue, preferably an optionally at least mono-substituted aryl residue.

3. Substituted γ-lactone compounds according to claim 1, characterised in that $R^2$ denotes an optionally at least mono-substituted, branched or unbranched $C_{1-6}$ alkyl residue.

4. Substituted γ-lactone compounds according to claim 1, characterised in that $R^3$ denotes an optionally at least mono-substituted aryl residue and $R^4$ denotes H.

5. Substituted γ-lactone compounds according claim 1:

3-(2-Chloro-4-fluoro-phenylamino)-5-(4-fluoro-phenyl)-5-methyl-dihydro-furan-2-one, 5-Methyl-3-(4-phenoxy-phenylamino)-5-phenyl-dihydro-furan-2-one, 3-(2-Chloro-phenylamino)-5-(4-fluoro-phenyl)-5-methyl-dihydro-furan-2-one, 3-(4-Chloro-2-methyl-phenylamino)-5-methyl-5-phenyl-dihydro-furan-2-one, 3-(2,4-Dichloro-phenylamino)-5-(4-fluoro-phenyl)-5-methyl-dihydro-furan-2-one, 3-(4-Chloro-3-trifluoromethyl-phenylamino)-5-methyl-5-phenyl-dihydro-furan-2-one, 3-(2,3-Dichloro-phenylamino)-5-(4-fluoro-phenyl)-5-methyl-dihydro-furan-2-one, 3-(4-Iodo-phenylamino)-5-methyl-5-phenyl-dihydro-furan-2-one, 3-(4-Chloro-2-fluoro-phenylamino)-5-(4-fluoro-phenyl)-5-methyl-dihydro-furan-2-one, 3-(2-Chloro-4-methyl-phenylamino)-5-methyl-5-phenyl-dihydro-furan-2-one, 3-(2-Chloro-4-methyl-phenylamino)-5-(4-fluoro-phenyl)-5-methyl-dihydro-furan-2-one, 3-(3,5-Dichloro-phenylamino)-5-methyl-5-phenyl-dihydro-furan-2-one, 3-(3,5-Dichloro-phenylamino)-5-(4-fluoro-phenyl)-5-methyl-dihydro-furan-2-one, 3-(4-Bromo-2-chloro-phenylamino)-5-(4-fluoro-phenyl)-5-methyl-dihydro-furan-2-one, 4-(5-Methyl-2-oxo-5-phenyl-tetrahydro-furan-3-ylamino)-benzonitrile, 5-(4-Chloro-phenyl)-3-(4-iodo-phenylamino)-5-methyl-dihydro-furan-2-one, 5-(4-Chloro-phenyl)-3-(2,4-dichloro-phenylamino)-5-methyl-dihydro-furan-2-one, 5-(4-Chloro-phenyl)-3-(2-chloro-phenylamino)-5-methyl-dihydro-furan-2-one, 3-(4-Chloro-2-methyl-phenylamino)-5-(4-chloro-phenyl)-5-methyl-dihydro-furan-2-one 3-(2-Chloro-4-fluoro-phenylamino)-5-(4-chloro-phenyl)-5-methyl-dihydro-furan-2-one, 3-(4-Chloro-2-fluoro-phenylamino)-5-(4-chloro-phenyl)-5-methyl-dihydro-furan-2-one, 3-(2-Chloro-4-methyl-phenylamino)-5-(4-chloro-phenyl)-5-methyl-dihydro-furan-2-one, 5-(4-Chloro-phenyl)-3-(2,3-dichloro-phenylamino)-5-methyl-dihydro-furan-2-one, 3-(4-Bromo-2-chloro-phenylamino)-5-(4-chloro-phenyl)-5-methyl-dihydro-furan-2-one, 5-(4-Chloro-phenyl)-3-(3,5-dichloro-phenylamino)-5-methyl-dihydro-furan-2-one, 3-(3,5-Dibromo-pyridin-2-ylamino)-5-methyl-5-phenyl-dihydro-furan-2-one, 5-(4-Chloro-phenyl)-3-(3,5-dichloro-pyridin-2-ylamino)-5-methyl-dihydro-furan-2-one, 5-(4-Chloro-phenyl)-5-methyl-3-(5-nitro-pyridin-2-ylamino)-dihydro-furan-2-one, 3-(3-Chloro-2-methyl-phenylamino)-5-(4-iodo-phenyl)-5-methyl-dihydro-furan-2-one, 5-(4-Bromo-phenyl)-3-(4-chloro-phenylamino)-5-methyl-dihydro-furan-2-one, 5-(3-Chloro-phenyl)-3-(4-chloro-phenylamino)-5-methyl-dihydro-furan-2-one, 3-(4-chloro-phenylamino)-5-(4-iodo-phenyl)-5-methyl-dihydro-furan-2-one, 5-(4-Bromo-phenyl)-3-(2-iodo-phenylamino)-5-methyl-dihydro-furan-2-one, 5-(3-Chloro-phenyl)-3-(2-iodo-phenylamino)-5-methyl-dihydro-furan-2-one, 5-(4-Iodo-phenyl)-3-(2-iodo-phenylamino)-5-methyl-dihydro-furan-2-one, 3-(2,4-Difluoro-phenylamino)-5-methyl-5-naphthalen-1-yl-dihydro-furan-2-one, 5-(4-Bromo-phenyl)-3-(4-iodo-phenylamino)-5-methyl-dihydro-furan-2-one, 5-(3-Chloro-phenyl)-3-(4-iodo-phenylamino)-5-methyl-dihydro-furan-2-one, 3-(4-Iodo-phenylamino)-5-methyl-5-naphthalen-1-yl-dihydro-furan-2-one, 5-(4-Bromo-phenyl)-3-(3,5-dichloro-phenylamino)-5-methyl-dihydro-furan-2-one, 5-(3-Chloro-phenyl)-3-(3,5-dichloro-phenylamino)-5-methyl-dihydro-furan-2-one, 3-(3,5-Dichloro-phenylamino)-5-(4-iodo-phenyl)-5-methyl-dihydro-furan-2-one, 3-(3,5-Dichloro-phenylamino)-5-methyl-5-naphthalen-1-yl-dihydro-furan-2-one, 5-(3-Chloro-phenyl)-5-methyl-3-phenylamino-dihydro-furan-2-one, 3-(2-Bromo-4-methyl-phenylamino)-5-(4-iodo-phenyl)-5-methyl-dihydro-furan-2-one, 3-(2-Bromo-4-methyl-phenylamino)-5-methyl-5-naphthalen-1-yl-dihydro-furan-2-one, 3-(5-Chloro-2-methyl-phenylamino)-5-methyl-5-(5,6,7,8-tetrahydro-naphthalen-2-yl)-dihydro-furan-2-one, 3-(4-Bromo-2-fluoro-phenylamino)-5-isopropyl-5-phenyl-dihydro-furan-2-one, 5-(2,5-Dimethoxy-phenyl)-5-methyl-3-(5-trifluoromethyl-pyridin-2-ylamino)-dihydro-furan-2-one, 5-(3,5-Dimethoxy-phenyl)-5-methyl-3-(5-trifluoromethyl-pyridin-2-ylamino)-dihydro-furan-2-one, 3-(3-Bromo-5-methyl-pyridin-2-ylamino)-5-(2-methoxy-phenyl)-5-methyl-dihydro-furan-2-one, 3-(3-Bromo-5-methyl-pyridin-2-ylamino)-5-(2,5-dimethoxy-phenyl)-5-methyl-dihydro-furan-2-one, 3-(3-Bromo-5-methyl-pyridin-2-ylamino)-5-(3,5-dimethoxy-phenyl)-5-methyl-dihydro-furan-2-one, 3-(5-Bromo-3-methyl-pyridin-2-ylamino)-5-(2-methoxy-phenyl)-5-methyl-dihydro-furan-2-one, 3-(2-Chloro-pyridin-3-ylamino)-5-(2-methoxy-phenyl)-5-methyl-dihydro-furan-2-one, 3-(5-Bromo-pyridin-2-ylamino)-5-(2,5-dimethoxy-phenyl)-5-methyl-dihydro-furan-2-one, 3-(3-Chloro-5-trifluoromethyl-pyridin-2-ylamino)-5-(2,5-dimethoxy-phenyl)-5-methyl-dihydro-furan-2-one, 5-(2-Methoxy-phenyl)-5-methyl-3-(pyridin-2-ylamino)-dihydro-furan-2-one, 3-[5-(2,5-Dimethoxy-phenyl)-5-methyl-2-oxo-tetrahydro-furan-3-ylamino]-pyrazole-4-carboxylic acid ethyl ester, 3-[5-(3-Bromo-phenyl)-5-methyl-2-oxo-tetrahydro-furan-3-ylamino]-pyrazole-4-carboxylic acid ethyl ester, 3-[5-(3-Bromo-phenyl)-5-methyl-2-oxo-tetrahydro-furan-3-ylamino]-5-methylsulfanyl-pyrazole-4-carbonitrile, 3-[5-(2,5-Dimethoxy-phenyl)-5-methyl-2-oxo-tetrahydro-furan-3-ylamino]-pyrazole-4-carbonitrile, 3-(4-Bromo-pyrazol-3-ylamino)-5-(3,5-dimethoxy-phenyl)-5-methyl-dihydro-furan-2-one, 3-(4-Bromo-5-phenyl-2H-pyrazol-3-ylamino)-5-(2-methoxy-phenyl)-5-methyl-dihydro-furan-2-one, 3-(8-Hydroxy-quinolin-2-ylamino)-5-(2-methoxy-phenyl)-5-methyl-dihydro-furan-2-one, 5-(2,5-Dimethoxy-phenyl)-3-(8-hydroxy-quinolin-2-ylamino)-5-methyl-dihydro-furan-2-one, 5-(2-Methoxy-phenyl)-5-methyl-3-(pyrazin-2-ylamino)-dihydro-furan-2-one, 5-(3-Bromo-phenyl)-5-methyl-3-(4-methyl-pyrimidin-2-ylamino)-dihydro-furan-2-one, 2-[5-(3,5-Dimethoxy-phenyl)-5-methyl-2-oxo-tetrahydro-furan-3-ylamino]-4-propyl-pyrimidine-5-carboxylic acid ethyl ester, 5-(2-Methoxy-phenyl)-5-methyl-3-(pyrimidin-2-ylamino)-dihydro-furan-2-one, 3-(4-Chloro-3-trifluoromethyl-phenylamino)-5-phenyl-5-propyl-dihydro-furan-2-one, 3-(2-Chloro-phenylamino)-5-phenyl-5-propyl-dihydro-furan-2-one, 3-(2-Chloro-4-fluoro-phenylamino)-5-phenyl-5-propyl-dihydro-furan-2-one, 3-(4-Chloro-2-fluoro-phenylamino)-5-phenyl-5-propyl-dihydro-furan-2-one, 3-(2-Chloro-4-methyl-phenylamino)-5-phenyl-5-propyl-dihydro-furan-2-one, 3-(2-Oxo-5-phenyl-5-propyl-tetrahydro-furan-3-ylamino)-pyrazole-4-carboxylic acid ethyl ester, 3-(5-Hydroxy-4-phenylazo-pyrazol-3-ylamino)-5-phenyl-5-propyl-dihydro-furan-2-one, 3-(4-Bromo-5-phenyl-pyrazol-3-ylamino)-5-phenyl-5-propyl-dihydro-furan-2-one, 5-Methylsulfanyl-3-(2-oxo-5-phenyl-5-propyl-tetrahydro-furan-3-ylamino)-pyrazole-4-carbonitrile, 3-(5-Butyl-2-oxo-5-phenyl-tetrahydro-furan-3-ylamino)-pyrazole-4-carboxylic acid ethyl ester, 5-Butyl-3-(5-hydroxy-4-phenylazo-pyrazol-3-ylamino)-5-phenyl-dihydro-furan-2-one, 3-(4-Bromo-5-phenyl-pyrazol-3-ylamino)-5-butyl-5-phenyl-dihydro-furan-2-one, 3-(5-Butyl-2-oxo-5-phenyl-tetrahydro-furan-3-ylamino)-5-methylsulfanyl-pyrazole-4-carbonitrile, 3-(5-Butyl-2-oxo-5-phenyl-tetrahydro-furan-3-ylamino)-pyrazole-4-carbonitrile, 5-Butyl-3-(2-phenox-phenylamino)-5-phenyl-dihydro-furan-2-one, 5-Biphenyl-4-yl-3-(2,4-dichloro-phenylamino)-5-methyl-dihydro-furan-2-one, 5-Biphenyl-4-yl-3-(2-chloro-phenylamino)-5-methyl-dihydro-furan-2-one, 5-Biphenyl-4-yl-3-(2-chloro-4-fluoro-phenylamino)-5-methyl-dihydro-furan-2-one, 3-(5-Biphenyl-4-yl-5-methyl-2-oxo-tetrahydro-furan-3-ylamino)-pyrazole-4-carboxylic acid ethyl ester, 5-Biphenyl-4-yl-3-(4-bromo-5-phenyl-pyrazol-3-ylamino)-5-methyl-dihydro-furan-2-one, 3-(3,5-Dichlorophenylamino)-5-methyl-5-phenyl-dihydrofuran-2-one, 3-(3,5-Dichlorophenylamino)-5-methyl-5-o-tolyl-dihydrofuran-2-one, 3-(3,5-Dichlorophenylamino)-5-(4-fluorophenyl)-5-methyl-dihydrofuran-2-one, 5-(2-Chlorophenyl)-3-(3,5-dichlorophenylamino)-5-methyl-dihydrofuran-2-one, 5-(4-Chlorophenyl)-3-(3,5-dichlorophenylamino)-5-methyl-dihydrofuran-2-one, 5-(3-Bromophenyl)-3-(3,5-dichlorophenylamino)-5-methyl-dihydrofuran-2-one, 5-(4-Bromophenyl)-3-(3,5-dichlorophenylamino)-5-methyl-dihydrofuran-2-one, 3-(3,5-Dichlorophenylamino)-5-(4-iodophenyl)-5-methyl-dihydrofuran-2-one, 3-(3,5-Dichlorophenylamino)-5-(2-methoxyphenyl)-5-methyl-dihydrofuran-2-one, 3-(3,5-Dichlorophenylamino)-5-(3-methoxyphenyl)-5-methyl-dihydrofuran-2-one, 3-(3,5-Dichlorophenylamino)-5-(4-methoxyphenyl)-5-methyl-dihydrofuran-2-one, 3-(3,5-Dichlorophenylamino)-5-(2,4-dimethoxyphenyl)-5-methyl-dihydrofuran-2-one, 3-(3,5-Dichlorophenylamino)-5-(2,5-dimethoxyphenyl)-5-methyl-dihydrofuran-2-one, 3-(3,5-Dichlorophenylamino)-5-(3,5-dimethoxyphenyl)-5-methyl-dihydrofuran-2-one, 5-(Biphenyl-4-yl-)3-(3,5-dichlorophenylamino)-5-methyl-dihydrofuran-2-one, 3-(3,5-Dichlorophenylamino)-5-ethyl-5-phenyl-dihydrofuran-2-one, 3-(3,5-Dichlorophenylamino)-5-phenyl-5-n-propyl-dihydrofuran-2-one, 5-n-Butyl-3-(3,5-dichlorophenylamino)-5-phenyl-dihydrofuran-2-one, 3-(3,5-Dichlorophenylamino)-7a-phenyl-hexahydrobenzofuran, 3-(3,5-Dichlorophenylamino)-7a-(3-methoxy-phenyl)-hexahydrobenzofuran-2-one and 3-(3,5-Dichlorophenylamino)-8a-(3-methoxy-phenyl)-octahydrocyclo-hepta[b]furan-2-one and the corresponding physiologically acceptable salts thereof, preferably the hydrochlorides thereof.

6. A process for the production of substituted γ-lactone compounds according to one of claim 1, characterised in that at least one amine component of the general formula II, in which the residue $R^1$ has the meaning according to claims 1 to 5, is reacted with glyoxalic acid and at least one alkene component of the general formula III, in which the residues $R^2$ to $R^4$ have the meaning according to claims 1 to 5, in the presence of at least one inorganic and/or organic acid in an organic solvent to yield at least one compound of the general formula I according to claims 1 to 5 and this is optionally purified using conventional methods and/or optionally isolated using conventional methods.

7. A process according to claim 6, characterised in that the glyoxalic acid is used in the form of the monohydrate thereof or in form of an aqueous solution.

8. A process according to claim 6, characterised in that trifluoroacetic acid is used as the organic acid.

9. A process according to one of claim 6, characterised in that the temperature during the reaction is 0 to 100° C., preferably 15 to 40° C.

10. A process according to one of claim 6, characterised in that the duration of the reaction is 0.25 to 12 hours.

11. A process for the production of substituted γ-lactone compounds according to claim 1, characterised in that at least one amine component of the general formula II, in which the residue $R^1$ has the meaning according to claim 1 is reacted with glyoxalic acid and at least one alkene component of the general formula III, in which the residues $R^2$ to $R^4$ have the meaning according to claim 1 in an organic solvent, optionally in the presence at least one inorganic and/or organic acid with microwave irradiation or with exposure to ultrasound, preferably with microwave irradiation, to yield at least one compound of the general formula I according to claim 1 and this is optionally purified using conventional methods and/or optionally isolated using conventinal methods.

12. A process according to claim 11, characterised in that the temperature during the reaction is 40 to 70° C., preferably 45 to 60° C.

13. A pharmaceutical preparation containing at least one substituted γ-lactone compound according to claim 1 and optionally physiologically acceptable auxiliary substances.

14. A pharmaceutical preparation according to claim 13 for combatting pain.

15. A pharmaceutical preparation according to claim 14 for combatting chronic pain.

16. A pharmaceutical preparation according to claim 14 for combatting neuropathic pain.

17. A pharmaceutical preparation according to claim 13 for the treatment of neurodegenerative diseases, preferably of Alzheimer's disease, Parkinson's disease or Huntington's chorea.

18. A pharmaceutical preparation according to claim 13 for the treatment of stroke.

19. A pharmaceutical preparation according to claim 13 for the treatment of cerebral ischaemia.

20. A pharmaceutical preparation according to claim 13 for the treatment of cerebral infarct.

21. A pharmaceutical preparation according to claim 13 for the treatment of cerebral oedema.

22. A pharmaceutical preparation according to claim 13 for anxiolysis.

23. A pharmaceutical preparation according to claim 13 for anaesthesia.

24. A pharmaceutical preparation according to claim 13 for the treatment of schizophrenia.

25. A pharmaceutical preparation according to claim 13 for the treatment of psychoses brought about by elevated amino acid levels.

26. A pharmaceutical preparation according to claim 13 for the treatment of AIDS dementia.

27. A pharmaceutical preparation according to claim 13 for the treatment of Tourette's syndrome.

28. A pharmaceutical preparation according to claim 13 for the treatment of inflammatory and/or allergic reactions.

29. A pharmaceutical preparation according to claim 13 for the treatment of depression.

30. A pharmaceutical preparation according to claim 13 for the treatment of mental health conditions.

31. A pharmaceutical preparation according to claim 13 for the treatment of epilepsy.

32. A pharmaceutical preparation according to claim 13 for the treatment of urinary incontinence.

33. A pharmaceutical preparation according to claim 13 for the treatment of pruritus.

34. A pharmaceutical preparation according to claim 13 for the treatment of tinnitus.

35. A pharmaceutical preparation according to claim 13 for the treatment of diarrhoea.

36. A method of treating pain comprising administering to a patient a pharmaceutically effective amount of a pharmaceutical composition comprising at least one substituted γ-lactone compound according to one of claim 1.

37. A method according to claim 36, wherein the pain is chronic pain.

38. A method according to claim 36, wherein the pain is neuropathic pain.

39. A method of treating a neurodegenerative disease comprising administering to a patient a pharmaceutically effective amount of a pharmaceutical composition comprising at least one substituted γ-lactone compound according to claim 1.

40. A method according to claim 39, wherein the neurodegenerative disease is Alzheimer's disease.

41. A method according to claim 39, wherein the neurodegenerative disease is Parkinson's disease.

42. A method according to claim 39, wherein the neurodegenerative disease is Huntington's chorea.

43. A method of treating migraine, stroke, cerebral ischaemia, cerebral infarct, cerebral oedema, schizophrenia, psychoses brought about by elevated amino acid levels, AIDS dementia, Tourette's syndrome, inflammatory and/or allergic reactions; depression, mental health conditions, epilepsy, urinary incontinence, pruritus, tinnitus, diarrhea or anxiety comprising administering to a patient a pharmaceutically effective amount of a pharmaceutical composition comprising at least one substituted γ-lactone compound according to claim 1.

44. A method of anesthetizing comprising administering to a patient a pharmaceutically effective amount of a pharmaceutical composition comprising at least one substituted γ-lactone compound according to claim 1.

* * * * *